US012797192B2

(12) United States Patent
Burke et al.

(10) Patent No.: US 12,797,192 B2
(45) Date of Patent: Nov. 17, 2026

(54) CATHETER DEVICE FOR DELIVERING A MEDICAL IMPLANT ALLOWING OVERTRAVEL OF A CAPSULE OF THE CATHETER DEVICE

(71) Applicant: BIOTRONIK AG, Buelach (CH)

(72) Inventors: Jeff Alan Burke, Fallbrook, CA (US); Andy Edward Denison, Temecula, CA (US); Markus Foerster, Auenstein (CH); Ole Blank, Zurich (CH)

(73) Assignee: BIOTRONIK AG, Buelach (CH)

( * ) Notice: Subject to any disclaimer, the term of this patent is extended or adjusted under 35 U.S.C. 154(b) by 642 days.

(21) Appl. No.: 18/264,522

(22) PCT Filed: Feb. 14, 2022

(86) PCT No.: PCT/EP2022/053512
§ 371 (c)(1),
(2) Date: Aug. 7, 2023

(87) PCT Pub. No.: WO2022/175202
PCT Pub. Date: Aug. 25, 2022

(65) Prior Publication Data

US 2024/0041599 A1 Feb. 8, 2024

Related U.S. Application Data

(60) Provisional application No. 63/150,324, filed on Feb. 17, 2021.

(30) Foreign Application Priority Data

Mar. 9, 2021 (EP) .................................... 21161475

(51) Int. Cl.
*A61F 2/24* (2006.01)
*A61F 2/95* (2013.01)

(52) U.S. Cl.
CPC .......... *A61F 2/2436* (2013.01); *A61F 2/9517* (2020.05); *A61F 2002/9534* (2013.01)

(58) Field of Classification Search
CPC .. A61F 2/2436; A61F 2/95; A61F 2002/9534; A61F 2/9517;
(Continued)

(56) References Cited

U.S. PATENT DOCUMENTS

2014/0067050 A1 3/2014 Costello et al.
2019/0021460 A1* 1/2019 You ........................ A45B 25/22
(Continued)

FOREIGN PATENT DOCUMENTS

CN 103603858 B * 3/2016

OTHER PUBLICATIONS

International Search Report from the corresponding International Patent Application No. PCT/EP2022/053512, dated Apr. 25, 2022.

*Primary Examiner* — Katrina M Stransky
*Assistant Examiner* — Renee Florencia Nerenberg
(74) *Attorney, Agent, or Firm* — Greer, Burns & Crain, Ltd.; Steven P. Fallon

(57) ABSTRACT

A catheter device for implanting a medical implant has a handle that includes a locking element configured to be moved from a first to a second state. The locking element limits a movement of a traveler and therewith of a capsule in a distal direction (D) in the first state. The locking element allows further movement of the traveler and therewith of the capsule in the distal direction in the second state.

9 Claims, 11 Drawing Sheets

(58) Field of Classification Search
CPC ...... A61B 2017/2833; A61B 2017/347; A61B 2017/2837; A61M 39/1011; A45B 25/16
See application file for complete search history.

(56) References Cited

U.S. PATENT DOCUMENTS

| | | | | |
|---|---|---|---|---|
| 2019/0083261 | A1* | 3/2019 | Perszyk ................ | A61F 2/2436 |
| 2020/0054452 | A1* | 2/2020 | Shipley ................ | A61F 2/2436 |

* cited by examiner

CATHETER DEVICE FOR DELIVERING A MEDICAL IMPLANT ALLOWING OVERTRAVEL OF A CAPSULE OF THE CATHETER DEVICE

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2022/053512, which was filed Feb. 14, 2022, which application claimed priority from U.S. Provisional Application 63/150,324, filed Feb. 17, 2021, and from European Patent Application Number 21161475.5, filed Mar. 9, 2021.

FIELD OF THE INVENTION

The field of the invention concerns catheter devices for implanting a medical implant, particularly self-expanding implants such as an occluding device, aortic grafts, a prosthetic heart valve, more particularly an aortic heart valve prosthesis (TAVI/TAVR), but also e.g., for an implantable leadless pacemaker.

BACKGROUND

Such a catheter device usually includes a capsule for receiving the implant when the latter is in a collapsed state, e.g., a crimped prosthetic heart valve such as a prosthetic aortic heart valve. The capsule covers the implant (e.g. a prosthetic aortic heart valve) that is positioned on a support element connected to an inner sheath of the catheter device while the capsule is connected to an outer sheath (the inner and outer sheaths may also be denoted as inner and outer shafts of the catheter).

Retraction of the outer sheath with respect to the inner sheath allows displacing the capsule with respect to the inner sheath and the support element so as to deploy and release said implant. With the catheter device of the present invention, an implant like a prosthetic aortic heart valve may be, e.g., only partially released and can be retracted into the capsule for the purpose of re-positioning the implant so that it can be deployed at a proper implantation site in a next attempt. Reinserting the implant into the capsule is commonly termed "resheathing" and is for example achievable by providing a connection of the implant to a connector connected to the inner sheath of the catheter device.

Catheter devices of the aforementioned kind, particularly for implantation of a self-expanding transcatheter aortic valve replacement (TAVR) prosthesis (or TAVI prosthesis), are challenging in multiple aspects. A typical drawback is the fact that during recapturing of the TAVI/TAVR implant the catheter is exposed to high axial loads. In challenging anatomies or disadvantageous circumstances, these loads can plastically deform the sheaths of the catheter, which can affect a resheathing of the implant to the extend that the capsule can no longer completely cover the implant. However, the withdrawal of the device from the implantation site/body is only considered safe if the capsule is fully closed, i.e., properly aligned with the catheter tip so that no gap is present between the tip and a distal edge of the capsule.

Typically, safety buttons are known in the prior art which are used to limit the uncovering of the prosthesis. Mechanisms of this kind are for instance described in U.S. Pat. Nos. 9,782,257 B2, 9,545,308 B2, 9,615,924 B2, 8,814,931 B2, 8,778,019 B2 and 8,926,693 B2.

SUMMARY OF THE INVENTION

A preferred catheter device for implanting a medical implant, particularly a TAVI/TAVR catheter device for a self-expanding aortic valve prosthesis, allows implanting an implant, particularly a prosthetic heart valve, in particular a self-expanding aortic valve prosthesis, with the ability to allow proper closing of the capsule for the purpose of covering the implant during a resheathing procedure even in case of a permanent compression of the outer sheath and/or a permanent elongation of the inner sheath due to axial loads that have acted on the catheter device during implantation of the implant.

A preferred catheter device for implanting a medical implant has a handle that includes a locking element configured to be moved from a first to a second state. The locking element limits a movement of a traveler and therewith of a capsule in a distal direction (D) in the first state. The locking element allows further movement of the traveler and therewith of the capsule in the distal direction in the second state.

BRIEF DESCRIPTION OF THE DRAWINGS

In the following, further features and advantages of the present invention are described in detail with reference to the Figures which show preferred embodiments of the catheter device according to the present invention, wherein.

DETAILED DESCRIPTION OF THE PREFERRED EMBODIMENTS

Figure 1:
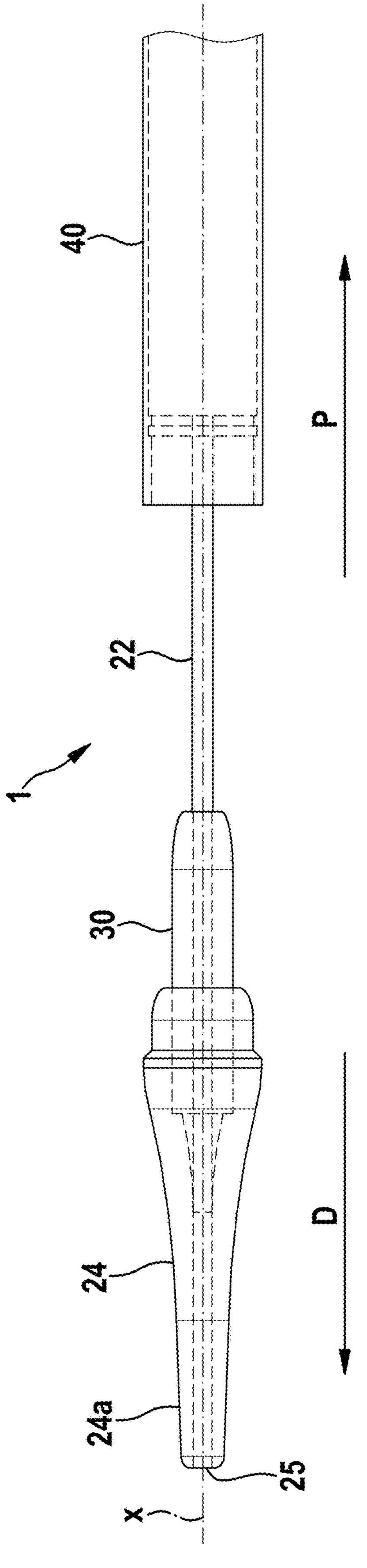
FIG. 1 shows a distal portion of an embodiment of a catheter device according to the present invention including a catheter tip and a capsule for covering the implant such that a distal end of the capsule is properly aligned with the catheter tip so that the capsule is arranged flush with the catheter tip and no portion of the implant sticks out of the capsule.

A preferred embodiment provides a catheter device for implanting a medical implant is disclosed, wherein the catheter device includes:

- an outer sheath extending along a longitudinal axis of the catheter device and surrounding a lumen of the outer sheath,
- an inner sheath extending along the longitudinal axis, wherein the inner sheath is arranged in the lumen of the outer sheath and connected to a support element for supporting the medical implant,
- a capsule connected to a distal end of the outer sheath for covering the medical implant when the medical implant is arranged on the support element,
- a handle including: a grip portion for manually holding the handle, a rotatable deployment knob, and a traveler, wherein the outer sheath is connected to the traveler, wherein the deployment knob includes a helical groove formed in an inside of the deployment knob, wherein the traveler engages into the helical groove of the deployment knob such that the traveler and thereby the outer sheath are moved in a proximal direction along the longitudinal axis with respect to the inner sheath when the deployment knob is rotated in a first rotation direction, so that the capsule is pulled away from the medical implant in the proximal direction to deploy the medical implant, and such that the traveler and thereby the outer sheath are moved in the distal direction along the longitudinal axis with respect to the inner sheath when the deployment knob is rotated in an opposite second rotation direction, so that the capsule is moved over the medical implant to cover the medical implant, wherein the handle includes a locking element that is configured to be manually moved by a user from a first state to a second state, wherein the locking element is configured to limit a movement of the traveler and therewith of the capsule in the distal direction in the first state and wherein the locking element is configured to allow further movement of the traveler and therewith of the capsule in the distal direction in the second state.

During recapturing of the TAVI/TAVR implant, the catheter is exposed to high axial loads. In challenging anatomies or disadvantageous circumstances, these loads can plastically deform the sheaths of the catheter, particularly said inner and outer sheaths. To ensure that the entire implant can still be covered by the capsule, additional travel of the potentially deformed outer sheath is required. Advantageously, this additional travel can be locked and enabled using the locking element. In addition, the mechanism preferably enables automatic resetting of the locking element after use and it may also provide feedback to the user that the locking element has been deactivated or reactivated.

Advantageously, the invention enables a further movement of the capsule in the distal direction so as to compensate the resulting length mismatch between the outer and inner sheath. With this additional travel, that is also denoted as “overtravel”, the outer sheath can be moved further in the distal direction than its original start position.

Furthermore, in the case that the sheaths do not deform in the procedure, the user could potentially close the capsule too far which would result in a sharp edge on the distal end. Therefore, the present invention includes a locking element so that the overtravel is only available when the locking element is moved to the second state. The activation and deactivation of the compensation feature is thus safe, detectable and reversible.

In the framework of the present invention, the notion “distal” refers to a portion or components of the catheter device that is remote from the handle or from the physician that operates the catheter device while the notion “proximal” refers to those portions or components that are closer to the handle or closer to the physician.

According to a preferred embodiment of the catheter device according to the present invention, the locking element is configured to set a limit to the movement of the traveler in the distal direction such that the capsule completely covers the implant when the traveler has reached this limit and the inner and the outer sheath have not yet been permanently deformed during usage of the catheter and each include their initial length in the direction of the longitudinal axis.

According to a further preferred embodiment, in the second state, the locking element is configured to allow further movement of the traveler and therewith of the capsule in the distal direction such that the implant is completely coverable by the capsule despite a permanent compression of the outer sheath or a permanent elongation of the inner sheath. Without the possibility of said further movement (i.e. overtravel) of the capsule, a gap between the catheter tip and the capsule could not be closed properly so that a resheathing procedure could not be successfully completed or would bear the risk of injuring the patient.

Furthermore, according to an embodiment of the present invention, the handle of the catheter device includes an elongated rod that is slidable along the longitudinal axis, wherein when the locking element is in its first state, the rod is configured to be pressed by the traveler against the locking element to limit the movement of the traveler (and therefore of the capsule) in the distal direction, wherein a first spring element connected to the traveler is arranged between the traveler and the rod and is pretensioned against the rod when the traveler presses against the locking element.

Preferably, the rod includes a proximal end portion having a concave face side to enclose a front side of the traveler in a form-fitting fashion when the traveler presses against the rod via said face side of the proximal end portion of the rod.

According to a further embodiment, the locking element is configured to release the rod when the locking element is moved from the first state to the second state, wherein the rod is pushed in the distal direction by the pretensioned first spring element that is allowed to expand when the locking element sets the rod free in the second state.

Furthermore, according to an embodiment, when the locking element is in the second state, the further movement (so-called overtravel) of the traveler in the distal direction caused by further rotation of the deployment knob in the first rotation direction pushes the rod against a stop provided on the handle which prevents any further movement of the traveler and therewith of the capsule in the distal direction. Now, the first spring element is pretensioned by the traveler against the rod, and a second spring element is pretensioned by the rod against a guiding member of the handle, which guiding member is configured to guide the sliding movement of the rod along the longitudinal axis and also forms said stop for the rod.

According to a further embodiment of the catheter device, the handle includes an actuating element configured to be manually actuated by a user, wherein the actuating element is operatively connected to the locking element, wherein the locking element is moved from the first state to the second state when the actuating element is actuated by the user. Particularly, the actuating element can be integrally connected to the locking element. Particularly, the actuating element can be a pushable button, wherein actuating the actuating element corresponds to manually pushing the button which causes the locking element to transition from the first state to the second state.

According to yet another embodiment of the catheter device, the handle includes a third spring element, wherein the third spring element is configured to be pretensioned against the locking element when the latter is moved from the first state to the second state. The third spring element thus provides a restoring force that allows moving the locking element back from the second state to the first state as will be described further below.

According to a further embodiment, the locking element includes an opening having a narrow portion and an adjacent wider portion, wherein the rod includes a distal portion including a narrow section having a diameter that is smaller than a diameter of an adjacent proximal portion of the rod (that connects to the proximal end portion of the rod) so that the rod forms a step, particularly a circumferential step, at said narrow section, wherein when the locking element is in the first state said narrow section of the rod is arranged in the narrow portion of the opening of the locking element and the rod is configured to be pressed by the traveler against the locking element with said step to prevent the movement of the traveler in the distal direction.

According to a further embodiment, when the locking element is moved from the first state to the second state, the rod becomes arranged in the wider portion of the opening of the locking element so that the step of the rod is allowed to move through the wider portion of the opening of the rod by the action of the pretensioned first spring element when the latter expands.

The deactivated locking element that allows movement of the rod in the distal direction in the second state can be automatically transferred back into the first state using the pretensioned third spring element when the capsule is opened again, i.e. by moving the outer sheath via the traveler in the proximal direction.

Particularly, when the traveler pushes the rod against the stop (which means that the maximal overtravel of the capsule has been realized) or when the second spring element is pretensioned, moving the traveler and therewith the capsule in the proximal direction (to again deploy the implant) causes the pretensioned second spring element to move the rod in the proximal direction, too, such that said narrow section of the rod moves back into the opening of the locking element at a certain position of the traveler which allows the third spring element to move the locking element back into the first state in which said section of the rod is in turn arranged in the narrow portion of the opening of the locking element.

The locking element has now returned to the first state and will limit further movement of the capsule in the distal direction until it is again moved to the second state by manually actuating, e.g. pushing, the actuating element (e.g. pushable button).

According to a further embodiment of the present invention, the deployment knob is rotatably supported on the guiding member of the handle that forms the stop for the rod and is also configured to guide the movement of the rod along the longitudinal axis.

The present invention enables further travel of a capsule 40 of a catheter device 1 so that the capsule 40 can properly resheath a partially deployed implant 100 even in case an outer and inner sheath 10, 20 of the catheter device 1 have been permanently deformed due to axial loads during the implantation procedure.

Figure 3:
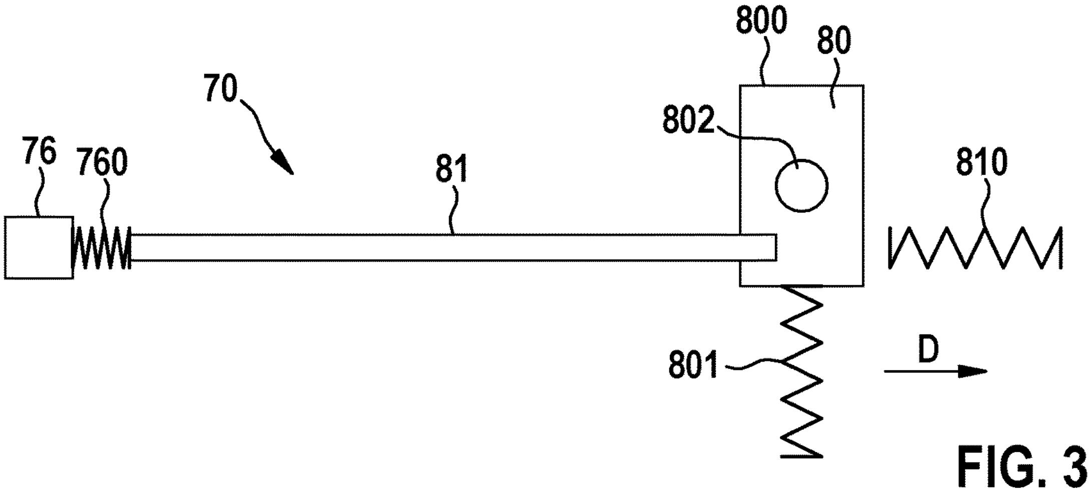
FIGS. 3 to 5 show schematical illustrations of a traveler of an embodiment of a catheter device according to the present invention and its interaction with a locking element for limiting/allowing a further movement of the capsule of the catheter device in the distal direction.
Figure 4:
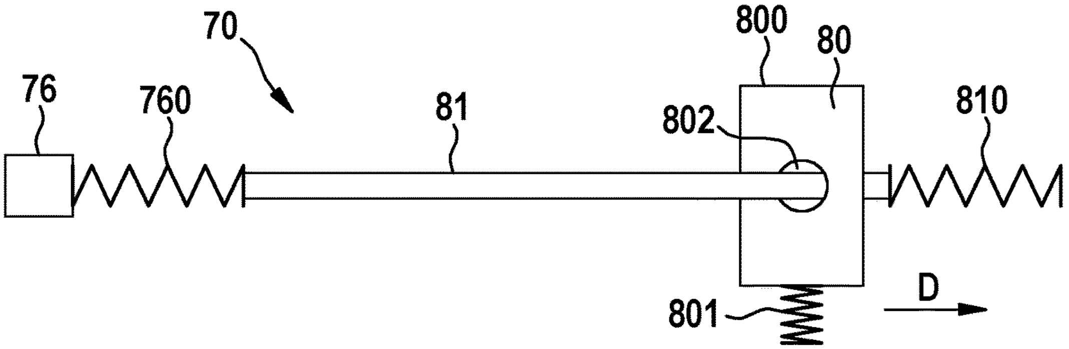
Figure 5:
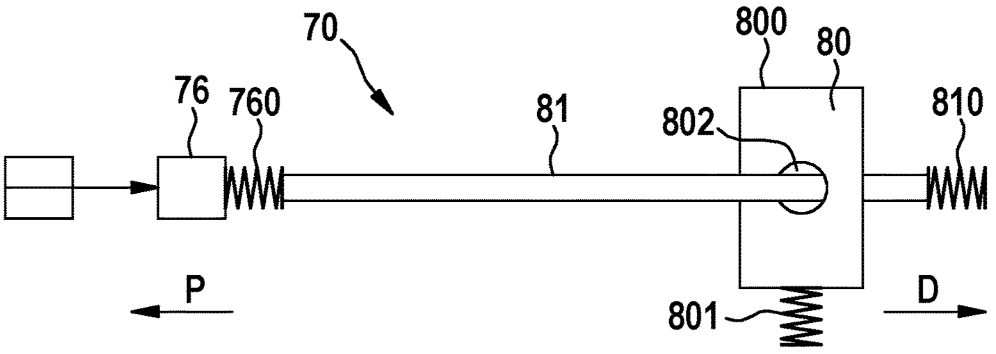

The principle mechanism of the invention is illustrated in FIGS. 3 to 5 and will be explained below in context with functions of the handle 70 and other components of the catheter device 1.

Figure 2:
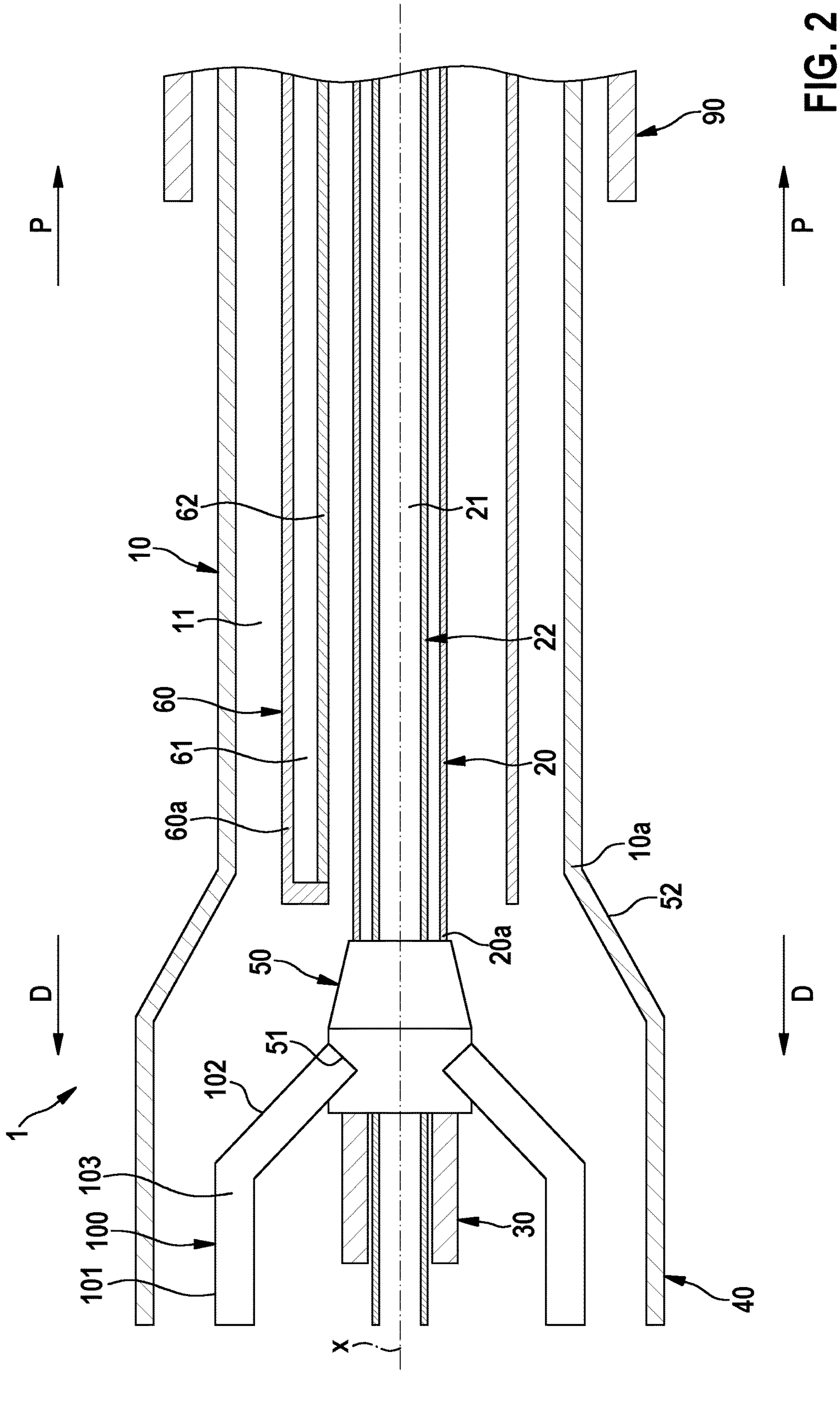
FIG. 2 shows a schematic cross sectional view of a portion of an embodiment of a catheter device according to the present invention, wherein the medical implant is covered by the capsule and connected to a connector at a distal end of the inner sheath; also shown is a stabilizing sheath that is connected to the grip portion of the handle (stabilizer) and a deflection sheath for adjusting the angular position of the capsule/medical implant.

Particularly, FIG. 1 shows a distal portion of an embodiment of a catheter device 1 according to the present invention, which includes a handle 70 that can be used to control functions of the catheter device 1. The handle is e.g. illustrated in FIGS. 6 to 13 and will be described in more detail further below. The catheter device 1 is configured to position a medical implant 100, particularly a prosthetic heart valve prosthesis such as a prosthetic aortic heart valve at an implantation site (e.g. anulus of a native aortic valve that is to be replaced). As indicated in FIG. 2, the implant 100 can include a self-expanding stent 101 with a tissue-based valve that can include three valve leaflets connected to the stent 101. FIG. 2 shows the stent 101 in a crimped state, wherein the leaflets (not shown in FIG. 2) can be made out of a biological tissue. The stent 101 preferably includes a plurality of interconnected struts 103, so that the stent 101 forms a circumferential scaffold including a plurality of lateral openings. The catheter device 1 can facilitate prosthesis delivery as well as axial positioning and angular orienting. Furthermore, the handle 70 can enable partial deployment, full deployment and recapturing (resheathing) of the medical implant/prosthetic heart valve 100.

Particularly, the handle 70 can be adapted to manipulate, particularly steer, four sheaths 20, 10, 60, and 90 as shown in FIG. 2, namely: an inner sheath 20 (also denoted as inner shaft 20) enclosing a guidewire lumen 21, a deflection sheath 60 (also denoted as deflection shaft 60) enclosing the inner sheath 20, an outer sheath 10 (also denoted as outer shaft 10) enclosing the inner sheath 20 and the deflection sheath 60, as well as a stabilizing sheath 90 (also denoted as stabilizing shaft or short “stabilizer” 90) enclosing a proximal section of the inner sheath 20, deflection sheath 60 and outer sheath 10. Particularly, each sheath 10, 20, 60 forms a tubular member.

As indicated in FIG. 2, the deflection sheath 60 can be deflected with a pulling member such as a pull wire 62 (for example a stainless-steel wire) that can be connected to a distal end section 60*a* of the deflection sheath 60. The pull wire 62 is arranged in a lumen of the deflection sheath 60. The deflection sheath 60 can include lateral openings so that the deflection sheath can be deflected by tensioning the pull wire 62. Particularly, in this way, the deflection sheath 60 can be deflected beyond 180°. In the letter case, the deflection sheath includes a u-shaped distal end section 60*a*.

The inner and the outer sheath 20, 10 can be moved relative to the deflection sheath 60 (and relative to the stabilizing sheath 90). Additionally, the outer sheath 10 can be moved relative to the inner sheath 20. The stabilizing sheath 90 is stationary and fixed to a grip portion 71 of the handle 70 (cf. FIGS. 6 to 13). The stabilizing sheath 90 does only bridge the movements of the other sheaths 10, 20, 60 to the anatomy of the patient and/or an introducer, if necessary. Particularly, the deflection sheath 60 is shorter than the inner and the outer sheath 20, 10. Further, a capsule 40 can be connected to a distal end 10*a* of the outer sheath 10 (e.g. via a capsule connector 52, cf. FIG. 2), wherein the capsule 40 can be larger in diameter (perpendicular to the longitudinal axis x along which the sheaths 10, 20, 60, 90 extend) than a proximal section of the outer sheath 10.

For delivery using the catheter device 1, the medical implant 100, here an aortic prosthetic heart valve 100, is placed on a support element 30 that is connected to a distal end section 20*a* of the inner sheath 20 and covered by the capsule 40. The support element 30 can be connected to the inner sheath 20 via a connector 50 to which the heart valve prosthesis 100 is releasably connectable for delivery to an implantation site when it is arranged in the capsule 40. The guidewire lumen 21 can be formed by a tubing 22 that protrudes out of the inner sheath 20 at the distal end 20*a* of the inner sheath 20, extends through the connector 50 and support element 30, and connects to a catheter tip 24 to which the tubing 22 is connected. Furthermore, the catheter tip 24 can include an opening 25 formed in a distal end 24*a* of the catheter tip 24, so that the guidewire can exit the guidewire lumen 21 via said opening 25 (cf. FIGS. 1 and 2).

The movements and functions of the catheter device 1 can be realized with the handle 70 of the catheter device 1 (cf. FIGS. 6 to 13), to this end, the handle 70 can include:

a stationary grip portion 71 configured for manually holding the handle 70 and to move the entire catheter device 1;

a rotatable deployment knob 72 for deploying and releasing the implant 100 by moving the outer sheath 10 in a proximal direction P with respect to the inner sheath 20 and the implant 100.

The handle 70 can further include actuating means for achieving a simultaneous movement of the inner and outer sheath 20, 10 as well as for deflecting the sheaths 10, 20 using the deflection sheath 60 and pull wire 62.

Preferably, the knob 72 is rotatable about the longitudinal axis x of the catheter device 1, along which axis x the handle 70 extends.

Furthermore, the grip portion 71 includes an opening 71*c* at a distal end 71*a* of the grip portion 71 through which all sheaths 10, 20, 60, 90 extend into the handle 70 at the distal end 71*a* of the grip portion 71 (the sheaths are not shown in FIGS. 6 to 13).

For deflecting the deflection sheath 60, an actuating means such as a deflection knob can be provided on the handle 70 that can be operatively connected to a distal end section 60*a* of the deflection sheath 60 via the pull wire 62, so that the deflection sheath 60 and thereby the inner and the outer sheath 20, 10 are deflected, i.e. bent, to adjust an angular orientation of the medical implant 100 when the deflection knob is rotated about the longitudinal axis x which causes tensioning or loosening of the pull wire 62 depending on the direction of the rotation.

Further, for moving the inner and the outer sheath 20, 10 simultaneously, the handle 70 can include a guiding member (also denoted as handle core) 75 (cf. FIGS. 6 to 13) that is movable with respect to the grip portion 71 along the longitudinal axis x, wherein the inner and the outer sheath 20, 10 are connected to the guiding member 75, and an actuating means such as an axial positioning knob can be operatively connected to the guiding member 75 such that the inner and the outer sheath 20, 10 are simultaneously moved with the guiding member 75 with respect to the grip portion 71 (and with respect to the deflection sheath 60 and stabilizing sheath 90) along the longitudinal axis x when the axial positioning knob is rotated about the longitudinal axis x.

Further, the handle 70 includes a traveler 76 (also denoted as outer sheath hub), wherein the outer sheath 10 is connected to the traveler 76, and wherein the deployment knob 72 is operatively connected to the traveler 76 such that the traveler 76 and thereby the outer sheath 10 are moved along the longitudinal axis x with respect to the inner sheath 20, and so as to deploy the medical implant 100 when the deployment knob 72 is rotated in a first rotation direction of the deployment knob 72 (cf. FIGS. 6 to 13).

If the physician is satisfied with the positioning of the catheter device 1, deployment of the prosthesis 100 is started by the physician. In this regard, an axial movement of the outer sheath 10 (and therewith of the capsule 40 and implant 100) in the proximal direction P relative to all other sheaths 20, 60, 90 and the grip portion 71 of handle 70 releases the implant 100; e.g. a prosthetic aortic heart valve. This movement of the outer sheath 10 can be controlled by the deployment knob 72 (cf. FIGS. 6 to 13), wherein rotation of the deployment knob 72 moves the traveler 76 to which the outer sheath 10 is connected. The movement of the outer sheath 10 and therewith of the capsule 40 in the proximal direction P releases the implant 100.

For releasing the implant 100 based on the above-described movement of the outer sheath 10 and capsule 40, the connector 50 connected to a distal end 20*a* of the inner sheath 20 can include a recess 51, wherein the at least one fastening element 102 of the medical implant 100 is engaged with the at least one recess 51 as long as the capsule 40 covers the at least one recess 51 of the connector 50 and the at least one fastening element 102 that engages with the at least one recess 51 when the prosthetic heart valve 100 is arranged on the support 30 (cf. FIG. 2). The at least one fastening element 102 can be formed by a portion of the self-expandable stent 101 of the prosthetic heart valve 100. Particularly, as shown in FIG. 2, the at least one fastening element 102 can be connected to at least one strut 103 of the stent 101 at a proximal end of the stent 101. For example, the stent 101 can include three such fastening elements 102. In this case, the connector 50 includes three corresponding recesses 51.

Once the capsule 40 is completely removed from the implant 100 and does no longer cover the at least one fastening element 102 and the corresponding recess 51 of the connector 50 (cf. lower part of FIG. 8) the at least one fastening element 102 disengages with the connector 50 due to the self-expanding property of the implant 100/stent 101, which releases the implant 100 at the implantation site. After complete deployment and release of the implant 100 from the catheter device 1, resheathing of the implant 100 is no longer possible.

In case the implant 100 is only partially deployed and still connected to the connector 50, resheathing of the implant 100 is possible. However, due to high axial loads acting on the inner and outer sheath 20, 10 during the implantation procedure, the sheaths 20, 10 can become permanently deformed in the direction of the longitudinal axis x during operation of the catheter device 1. This usually corresponds to a compression of the outer sheath 10 and an elongation of the inner sheath 10; which means that it is no longer possible to properly close the capsule 40, i.e., to completely cover the implant 100 with the capsule 40. Typically, a gap can result between the tip 24 and a distal edge of the capsule 40 which means that the resheathing cannot be properly completed.

In order to prevent this outcome, the present invention provides the capsule 40 with an additional travel which is denoted as overtravel and corresponds to a further movement of the capsule 40 in the distal direction D past the initial limit of the capsule 40.

As shown in FIGS. 3 to 5, in order to achieve this additional travel, the movement of the outer sheath 10 and therewith of the capsule 40 is coupled via e.g. the traveler 76 to an elongated rod 81 of the handle 70.

With the axial movement in the distal direction D during closing of the capsule 40, the rod 80 is reaching a rigid barrier in form of a locking element 80 which is inhibiting further axial travel of the rod 81 and therewith of the traveler 76 in the distal direction D. A first spring element 706 between the traveler 76 and the rod 81 is loaded in this position (cf. FIG. 3).

The locking element 80 can be configured to allow passage of the rod 81 through an opening 802 and can be configured to include a push button 800 for moving the locking element 80 perpendicular to the longitudinal axis x/distal direction D. The pushing of the locking element 80 loads the third spring element 801. Once the barrier 80 is removed, the rod 81 is pushed forward by the pretensioned first spring element 760. According to an embodiment of the present invention, the unloading of the first spring element 760 is audible and the change in position of the push button 800 is visible (cf. FIG. 4).

Subsequently, the user can move the traveler 76 and therewith the outer sheath 10 and capsule 40 forward in the distal direction D and the rod 81 moves further through the opening 802 of the locking element/barrier 80. Using this overtravel, the user carefully closes the capsule 40 (capsule 40 properly aligned with the atraumatic tip 24 in a gapless fashion) and thereby pretensions the first spring element 760 as well as the second spring element 810 (cf. FIG. 5).

In the next step, in case the user is satisfied with the repositioned implant, the user is releasing the implant 100 again. The outer sheath 10 is moved in the opposite direction (proximal direction P) and the implant 100 is deployed. After this second deployment it is possible that the user needs to resheath the prosthesis again. Therefore, the already used locking mechanism must be re-activated.

This lock reactivation is achieved by the second and third spring element 810, 801. Starting from FIG. 5, the traveler 76 that connects to the outer sheath 10 and capsule 40 is now being moved in the proximal direction P (i.e. to the left). This allows the second spring element 810 to force the rod 81 to follow the traveler 76. Once the rod 81 has traveled past the locking element/barrier 80, the third spring element 801 pushes the locking element/barrier 80 back into the locked position (first state). According to an embodiment, the relaxation of the third spring element 801 is audible and the position change of the locking element/barrier 80 is visible via the push button 800. With this mechanism, the lock/unlock cycle can be repeated.

This mechanism can be integrated in various ways into a handle 70 of a catheter device 1. In the following an embodiment of such an integration is described with reference to FIGS. 6 to 13.

Figure 6:
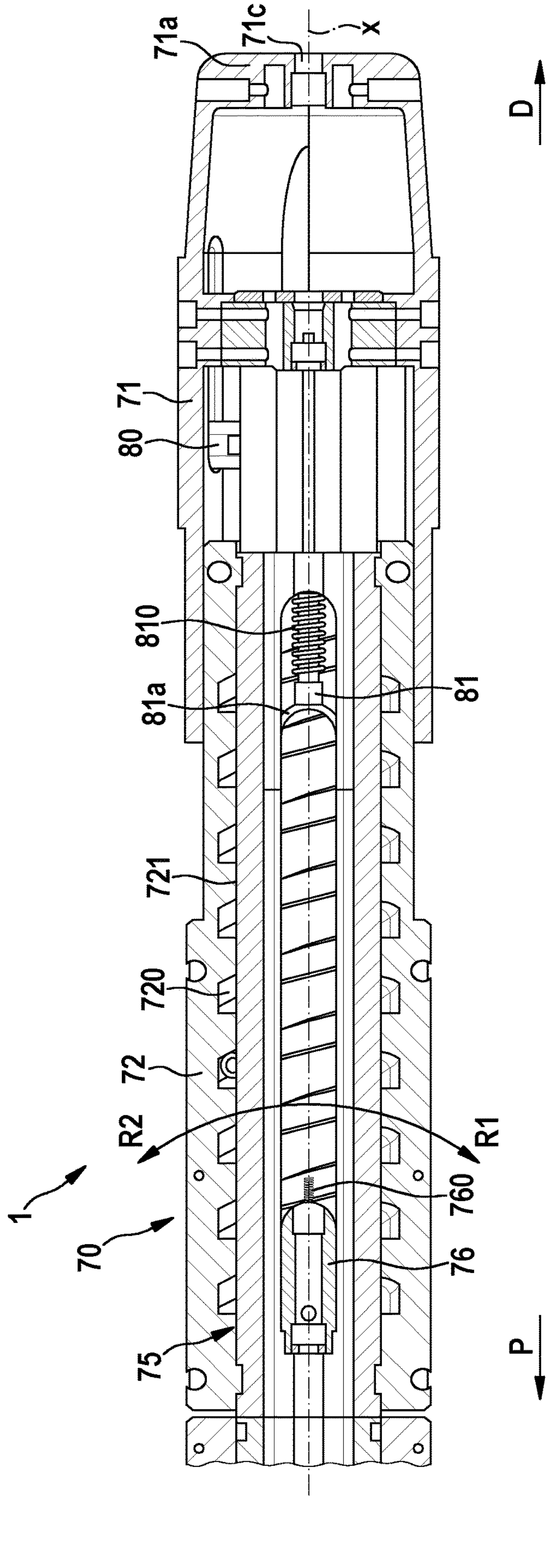
FIG. 6 shows a cross-sectional view of a handle of an embodiment of a catheter device according to the present invention including a locking element for limiting or allowing a further movement of the traveler of the handle in the distal direction, wherein the traveler is in a proximal position.
Figure 7:
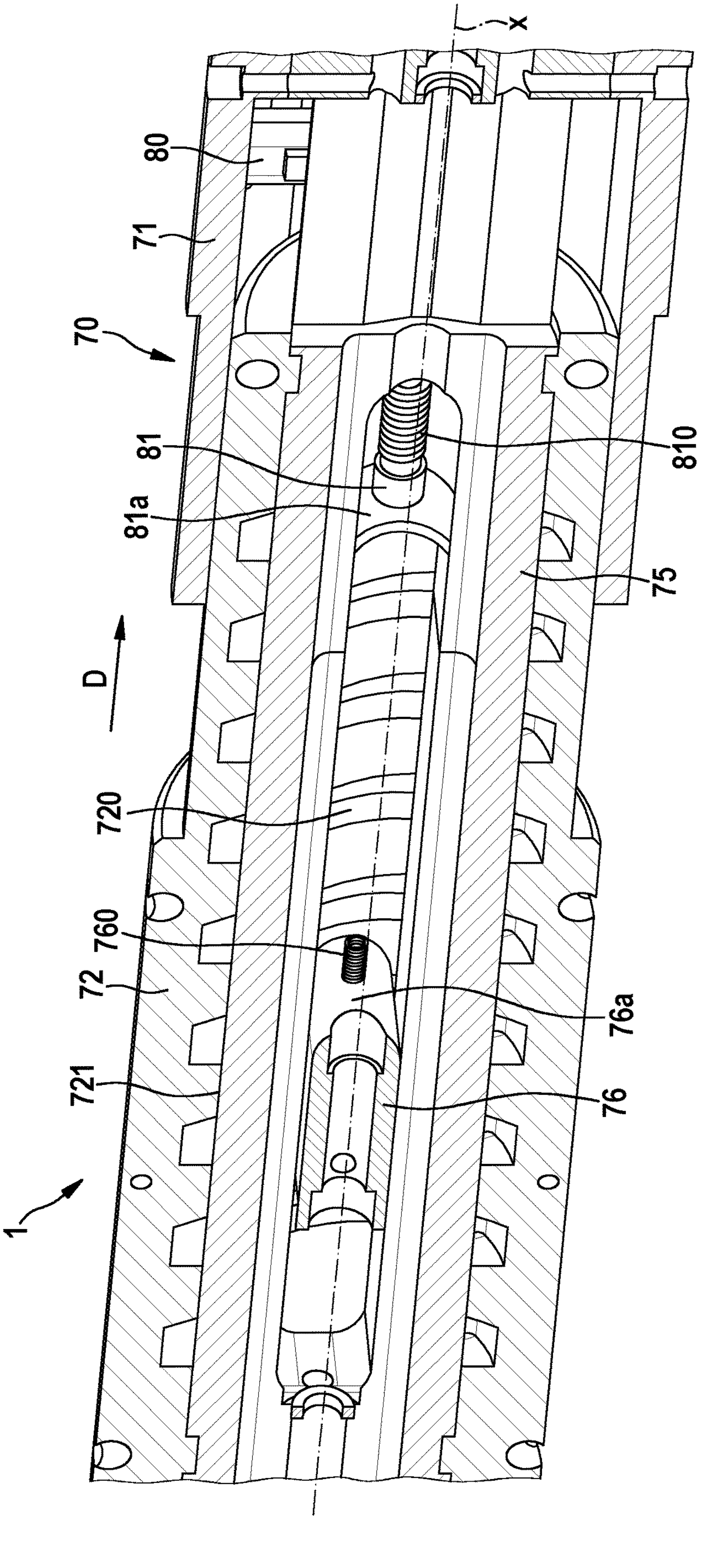
FIG. 7 shows a perspective cross-sectional view of the handle shown in FIG. 6, wherein the traveler and thus the capsule are not fully retracted.

As shown in FIG. 6 in conjunction with FIGS. 1 and 2, the catheter device 1 includes an outer sheath 10 extending along a longitudinal axis x of the catheter device 1 and surrounding a lumen 11 of the outer sheath 10, an inner sheath 20 extending along the longitudinal axis x, wherein the inner sheath 20 is arranged in the lumen 11 of the outer sheath 10 and connected to a support element 30 for supporting the medical implant 100, a capsule 40 connected to a distal end 10*a* of the outer sheath 10 for covering the medical implant 100 when the medical implant 100 is arranged on the support element 30, a handle 70 including: a grip portion 71 for manually holding the handle 70, a rotatable deployment knob 72, and a traveler 76, wherein the outer sheath 10 (cf. FIG. 2, not shown in FIGS. 6 to 13) is connected to the traveler 76, wherein the deployment knob 72 includes a helical groove 720 formed in an inside 721 of the deployment knob 72, wherein the traveler 76 engages into the helical groove 720 of the deployment knob 72 such that the traveler 76 and thereby the outer sheath 10 are moved in a proximal direction P along the longitudinal axis x with respect to the inner sheath 20 when the deployment knob 72 is rotated in a first rotation direction R1, so that the capsule 40 is pulled away from the medical implant 100 in the proximal direction P to deploy the medical implant 100, and such that the traveler 76 and thereby the outer sheath 10 are moved in the distal direction D along the longitudinal axis x with respect to the inner sheath 20 when the deployment knob 72 is rotated in an opposite second rotation direction R2 (cf. FIG. 6), so that the capsule 40 is moved over the medical implant 100 to cover the medical implant 100. Furthermore, the handle 70 includes a locking element 80 that is configured to be moved from a first to a second state, wherein the locking element 80 limits a movement of the traveler 76 and therewith of the capsule 40 in the distal direction D in the first state, and wherein the locking element 80 allows further movement of the traveler 76 and therewith of the capsule 40 in the distal direction D in the second state. Particularly, the inner sheath (cf. FIG. 2, not shown in FIGS. 6 to 13) is stationary during the deploy/resheath cycle which can include an unlock/lock cycle.

As stated above, the deploy traveler 76 is connected to the outer sheath 10 and is moved in axial direction x by the rotation of the deployment knob 72. On the front side 76*a* of the traveler 76, a first spring element 706 is connected to the traveler 76 that protrudes from the front side 76*a* in the distal direction D and moves with the traveler 76 (cf. FIG. 7).

Particularly, the traveler 76 moves in the distal direction D (to the right) until it reaches an elongated slidable rod 81 that is also denoted as overtravel traveler. The state depicted in FIG. 8 and FIG. 9 essentially corresponds to the state shown in FIG. 3.

Figure 8:
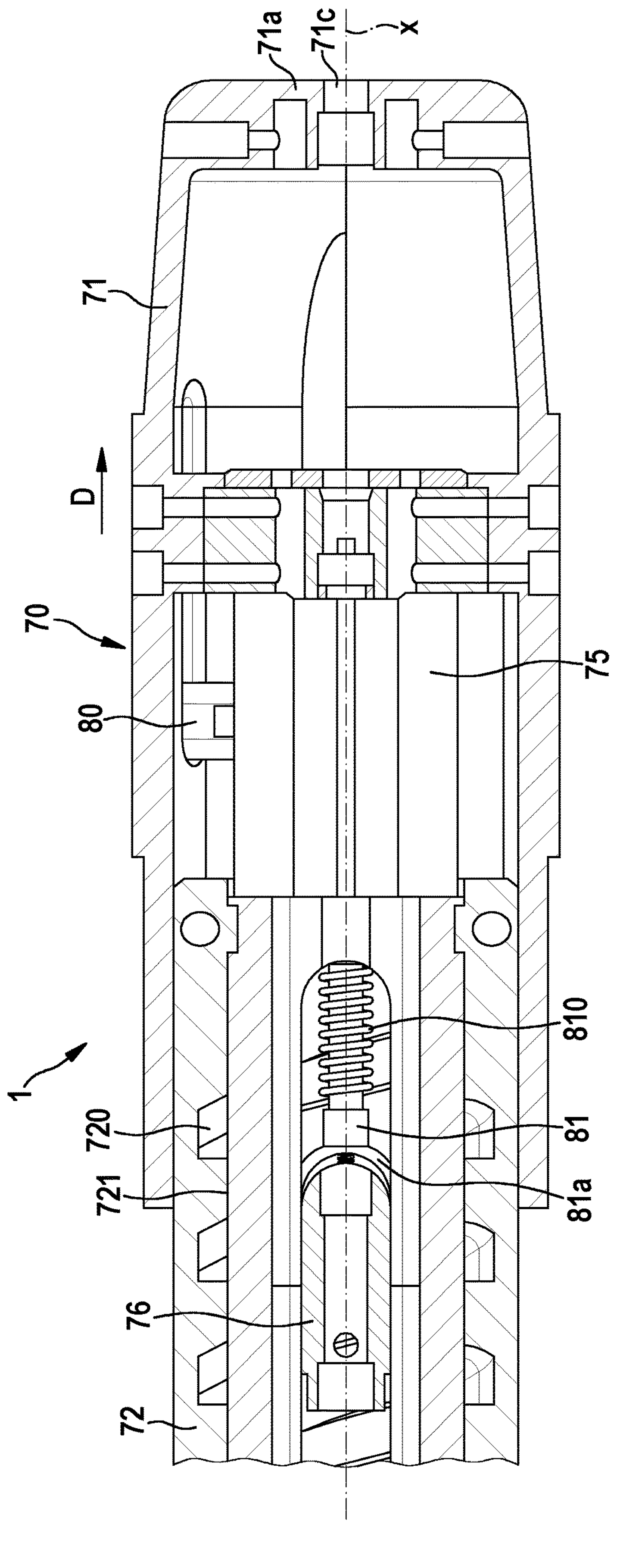
FIG. 8 shows a cross-sectional view of the handle shown in FIGS. 6 and 7, wherein further movement of the traveler is limited by the locking element; in case of non-deformed outer and inner sheaths this position of the capsule corresponds to the closed state of the capsule where the implant is fully covered and can be moved to the implantation site using the catheter device.

When the traveler 76 has reached the rod 81 as shown in FIG. 8, the front side 76*a* is particularly enclosed in a form-fitting manner by a concave face side of a proximal end portion 81*a* of the rod 81. The first spring element 760 is therefore fully loaded, i.e., pretensioned against the rod 81. The second spring element 810 that surrounds the rod 81 is not yet loaded since the rod 81 is stopped by the locking element 80 as shown in FIG. 9.

Figure 9:
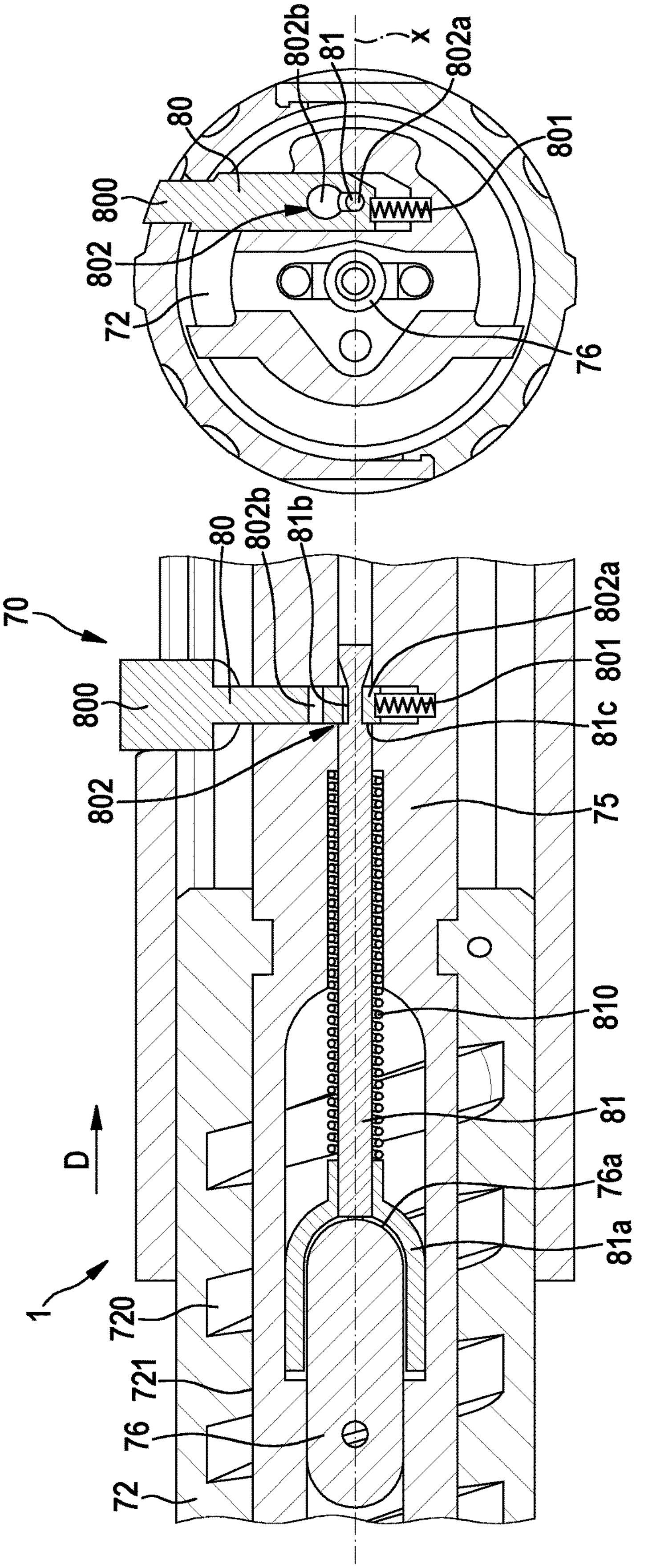
FIG. 9 shows further views of the state of the handle of the catheter device shown in FIG. 8.

FIG. 9 shows a side (left) and a front (right) view of the lock mechanism. The rod 81 is pushed in the distal direction D by the traveler 76/first spring element 760 (not visible in FIG. 9). The locking element 80 is blocking the path of the rod 81, wherein a third spring element 801 below the locking element 80 is holding the locking element 80 in the default first state corresponding to the locked state of the locking element 80.

Particularly, the locking element 80 includes an opening 802 having a narrow portion 802*a* and an adjacent wider portion 802*b*. Correspondingly, the rod 81 includes a distal portion including a narrow section 81*b* having a diameter that is smaller than a diameter of an adjacent proximal portion of the rod 81 so that the rod 81 forms a step 81*c* (e.g. a circumferential step) at said section 81*b*, wherein when the locking element 80 is in the first (locked) state said narrow section 81*b* of the rod 81 is arranged in the narrow portion 802*a* of the opening 802 and the rod 81 cannot be moved further through the opening 802 since the step 81*c* butts against the locking element 80, namely against an edge of the narrow portion 802*a* of the opening 802.

Figure 10:
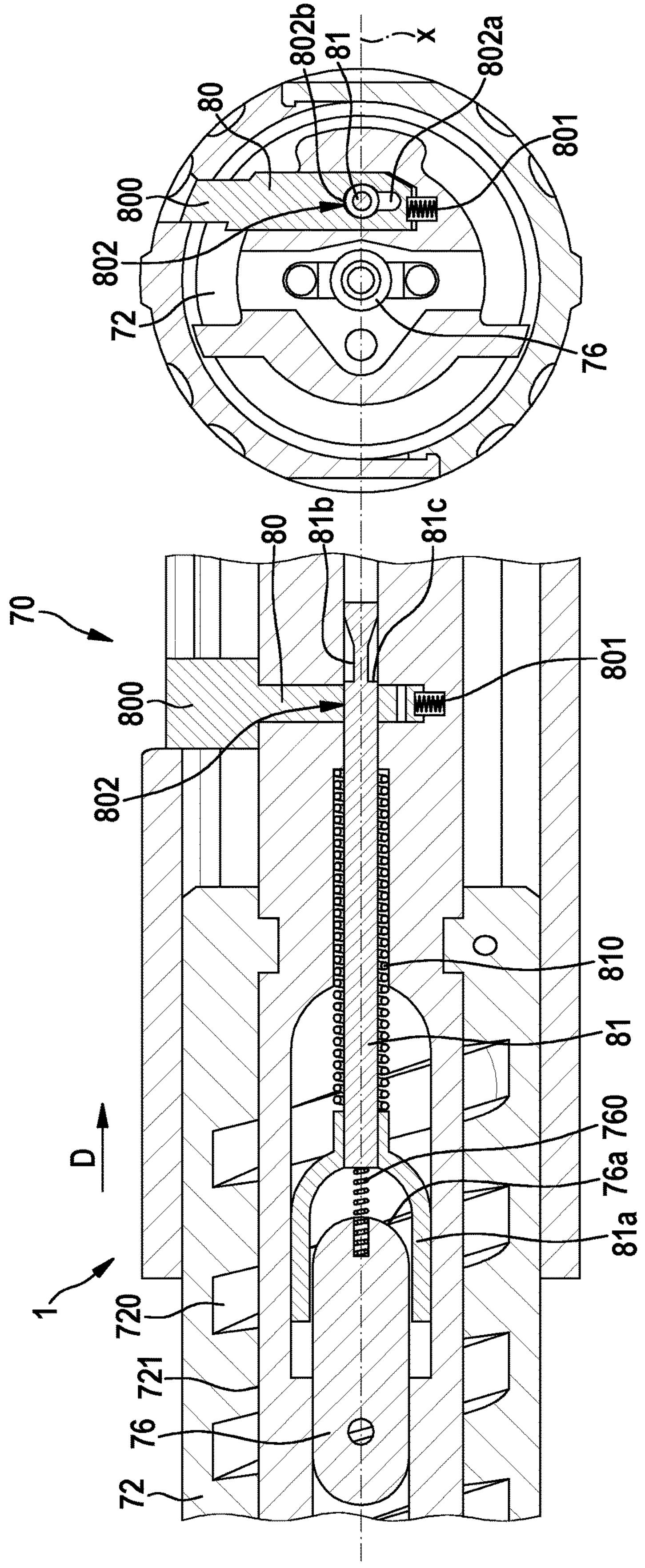
FIG. 10 shows the situation where—compared to FIGS. 8 and 9—the locking element has been brought from the first state to the second state such that the locking element releases the rod and the pretensioned first spring element pushes the rod further into the opening of the locking element which keeps the locking element in the second state and allows further movement of the traveler and capsule in the distal direction.

According to FIG. 10, the additional travel of the traveler 76/capsule 40 is activated by pushing down a top side 800 of the locking element 80 which forms a push button 800. The corresponding downward movement of the locking element 80 arranges the rod 81 in the wider portion 802*b* of the opening 802 which clears the path for the rod 81 to travel through, since the wider portion 802*b* includes a diameter that does not allow blocking of the step 81*c* of the rod 81.

Now, with the locking element 80 being in the second (open) state, the traveler's 76 first spring element 706 pushes the rod 81 forward through the opening 802 of the locking element 80. Particularly, the user can hear/feel the jump of the rod 81 as feedback for successful unlocking. Due to the button 800/locking element 80 being pushed into the second state, the third spring element 801 is now loaded.

The elongated rod 81 can now travel freely through the wider portion 802*b* of the opening 802 of the locking element 80. The distal movement of the deploy traveler 76 (overtravel) can be used by rotating the deployment knob 72 further in the first rotation direction R1 until the first spring element 760 and the second spring element 810 are fully compressed or the rod 81 hits a stop 83 provided on the handle 70.

Figure 11:
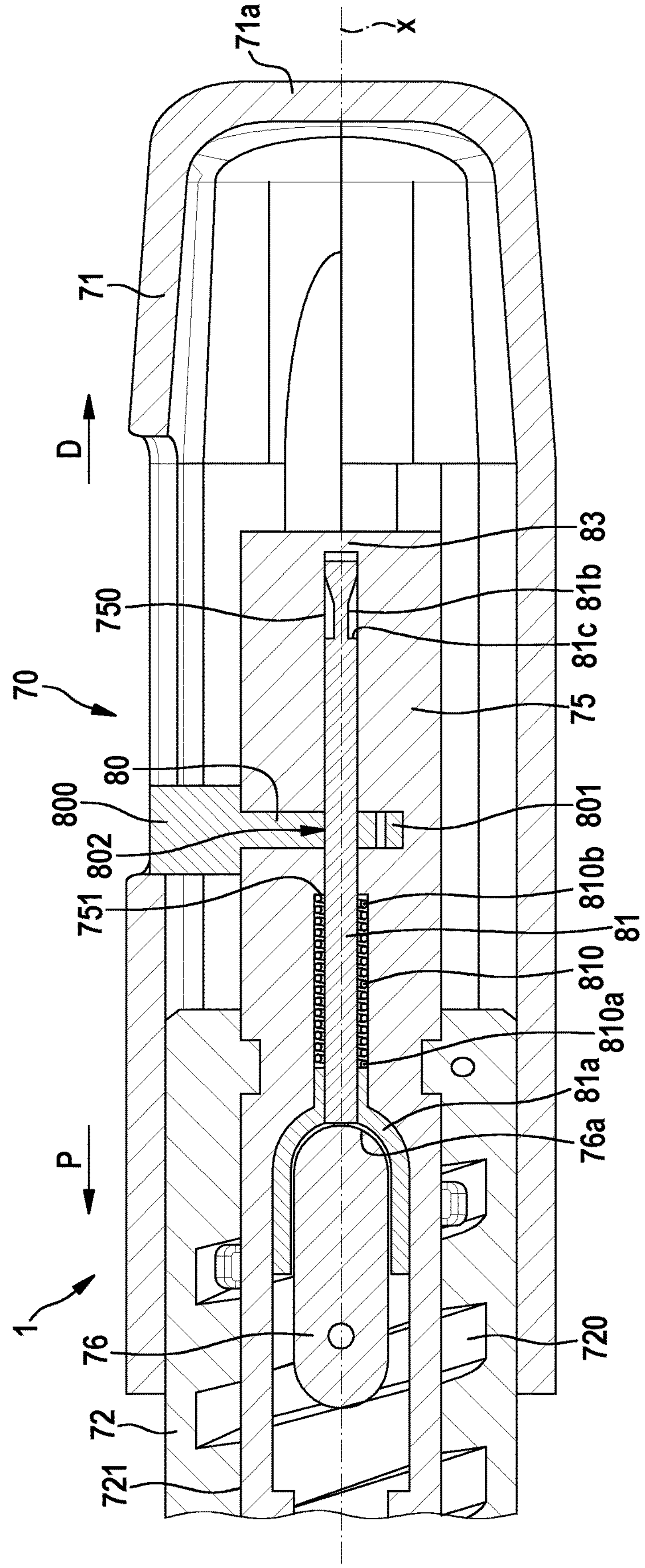
FIG. 11 shows a cross sectional view of the handle of the catheter device shown in FIGS. 6 to 10, wherein the further movement of the traveler in the distal direction is stopped by the rod that butts against a stop of the handle (i.e. maximal overtravel of the capsule has been reached)
Figure 12:
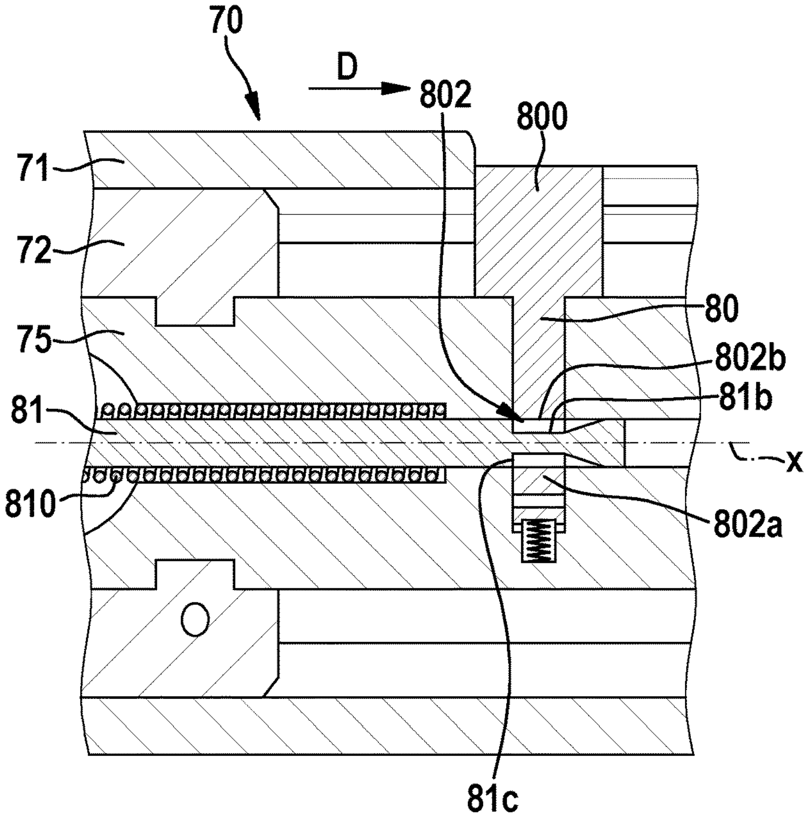
FIGS. 12 to 13 show the return of the locking element from the second state to the first state by moving the traveler in the proximal direction, which due to the action of the second spring element cause a narrow section of the rod to be again positioned in a narrow portion of an opening of the locking element so that the locking element can be moved into its first position by the pretensioned third spring element.
Figure 12:
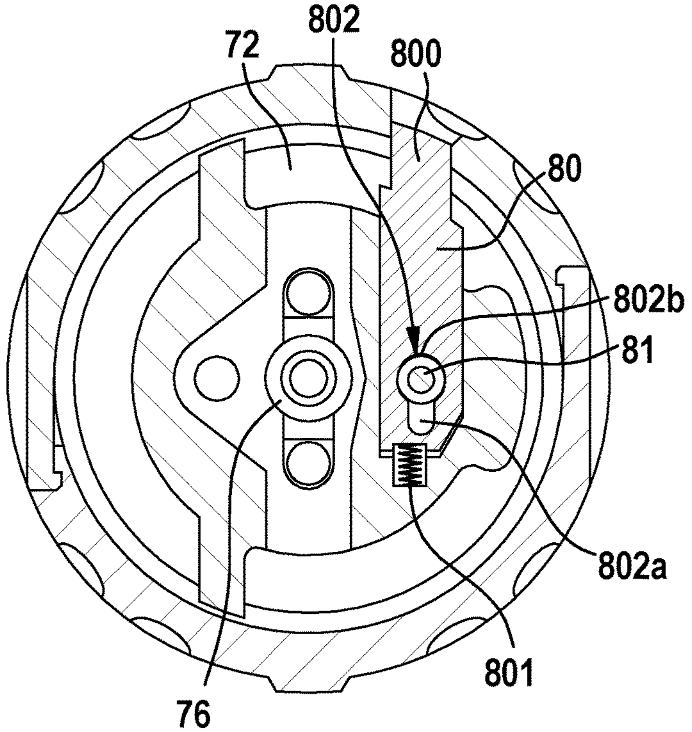
Figure 13:
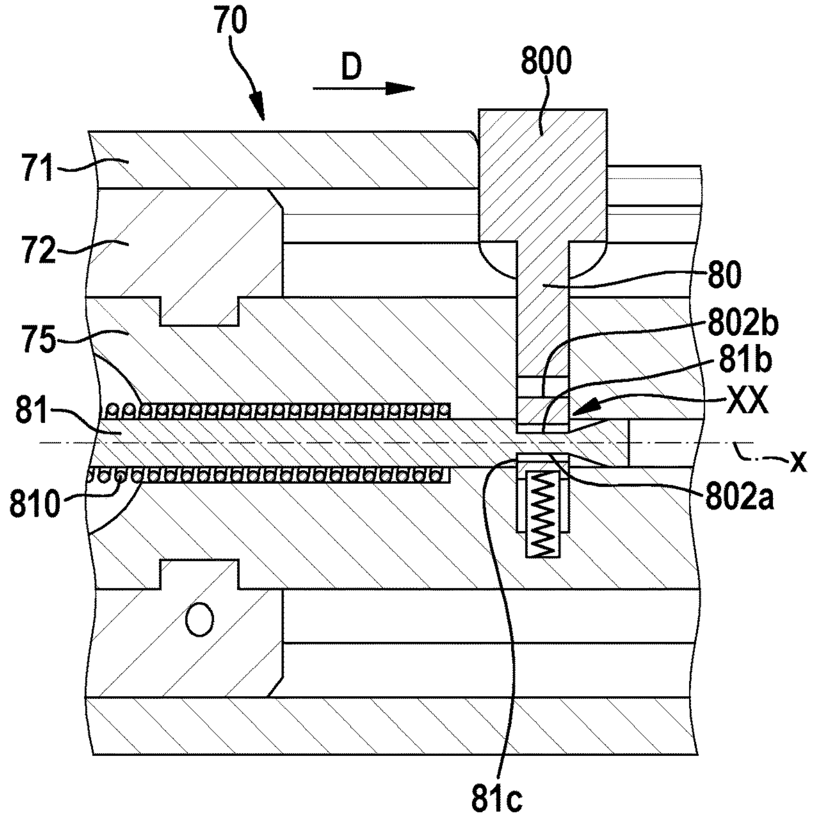
Figure 13:
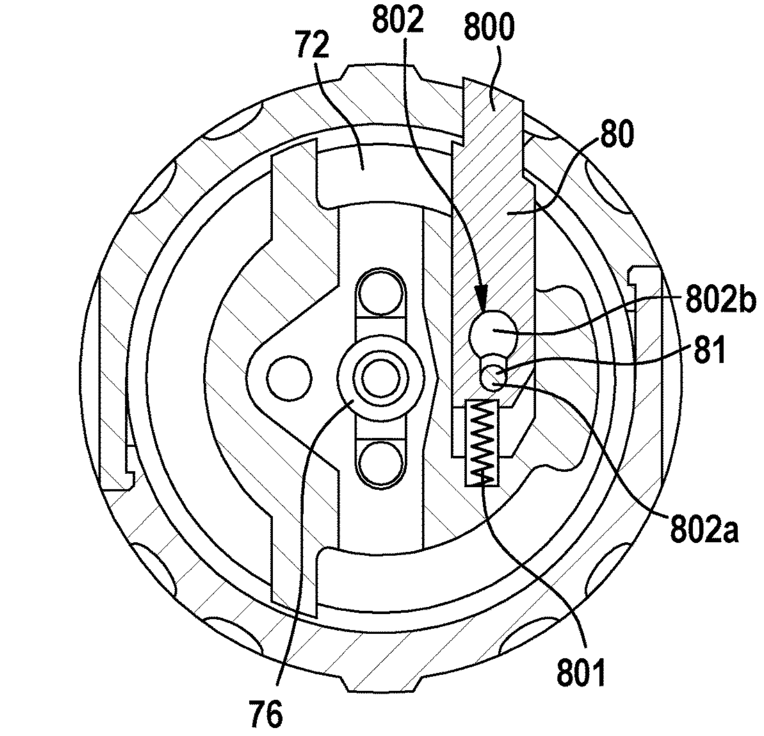

Particularly, the locking element 80 being in the second (unlocked) state allows a specific extra overtravel. According to an embodiment, this overtravel is in the range from 10 mm to 30 mm. Particularly, the overtravel amounts to 20 mm in an embodiment. FIG. 11 shows the maximum overtravel/possible further movement of the capsule 40. In this case the first and the second spring element 760, 810 are fully compressed and the rod 81 reaches the stop 83.

Particularly, as shown in FIG. 11, the rod 81 is guided by a guiding member 75 that is also denoted as handle core 75. The guiding member 75 includes an elongated hole 750 into which the rod 81 extends and which guides the rod 81 upon its movement long the longitudinal axis x. A bottom 83 of the hole 750 forms the hard stop for the rod 81. The second spring element 810 that surrounds the rod 81 butts with a first end 810*a* against a circumferential step 751 formed on an internal surface of the hole 750, and with a second end 810*b* against the proximal end portion 81*a* of the rod 81. In this way, the pretensioned second spring element 810 can push the rod 81 in the proximal direction P in case the traveler 76 is moved back in the proximal direction P with the locking element 80 being in the second (open) state.

After successful recapturing of the implant 100 with the help of the overtravel of the capsule 40, the user opens the capsule 40 (i.e. moves it proximal) for a second deploy attempt. The deploy traveler 76 then moves in the proximal direction (to the left in FIG. 11) and the second spring element 810 ensures that the entire rod 81 is moving proximal, too. If the traveler 76 reaches the initial position before the overtravel activation, the narrow section 81*b* of the rod 81 is aligned with the opening 802 of the locking element 80 again. The third spring element 801 can thus push the locking element 80 back up in its original position (first state). This means that the narrow section 81*b* of the rod shifts to the narrow portion 802*a* of the opening 802 of the locking element 80 such that the rod 81 presses with its step 81*c* against the locking member 80 in case an attempt to move the traveler 76 further distal is made. The locking element/mechanism 80 can now be reused.

Particularly, the movement of the locking element 80 is visible as well as audible.

The solution according to the present invention combines increased safety with good usability. Particularly, the locking element can be operated in a stable manner and its states can be detected either visually and/or acoustically.

In view of all the foregoing disclosure, the present invention also provides for the following embodiments:

A. A catheter device (1) for implanting a medical implant (100), including:
- an outer sheath (10) extending along a longitudinal axis (x) of the catheter device (1) and surrounding a lumen (11) of the outer sheath (10),
- an inner sheath (20) extending along the longitudinal axis (x), wherein the inner sheath (20) is arranged in the lumen (11) of the outer sheath (10) and connected to a support element (30) for supporting the medical implant (100) or to a connector (50),
- a capsule (40) connected to a distal end (10*a*) of the outer sheath (10) for covering the medical implant (100) when the medical implant (100) is arranged on the support element (30) or the connector (50),
- a handle (70) including: a grip portion (71) for manually holding the handle (70), a rotatable deployment knob (72), and a traveler (76), wherein the outer sheath (10) is connected to the traveler (76), wherein the deployment knob (72) includes a helical groove (720) formed in an inside (721) of the deployment knob (72), wherein the traveler (76) engages into the helical groove (720) of the deployment knob (72) such that the traveler (76) and thereby the outer sheath (10) are moved in a proximal direction (P) along the longitudinal axis (x) with respect to the inner sheath (20) when the deployment knob (72) is rotated in a first rotation direction (R1), so that the capsule (40) is pulled away from the medical implant (100) in the proximal direction (P) to deploy the medical implant (100), and such that the traveler (76) and thereby the outer sheath (10) are moved in the distal direction (D) along the longitudinal axis (x) with respect to the inner sheath (20) when the deployment knob (72) is rotated in an opposite second rotation direction (R2), so that the capsule (40) is moved over the medical implant (100) to cover the medical implant (100), wherein the handle (70) includes a locking element (80) that is configured to be moved from a first to a second state, wherein the locking element (80) limits a movement of the traveler (76) and therewith of the capsule (40) in the distal direction (D) in the first state, and wherein the locking element (80) allows a further movement of the traveler (76) and therewith of the capsule (40) in the distal direction (D) in the second state.

B. The catheter device according to embodiment A, wherein in the first state the locking element (80) is configured to set a limit to the movement of the traveler (76) in the distal direction (D) such that the capsule (40) completely covers the implant (100) when the traveler is positioned at said limit and the inner and the outer sheath (20, 10) have not yet been permanently deformed during operation of the catheter device (1) and each include their initial length in the direction of the longitudinal axis (x).

C. The catheter device according to embodiment A or B, wherein in the second state the locking element (80) is configured to allow further movement of the traveler (76) and therewith of the capsule (40) in the distal direction (D) such that the implant is completely coverable by the capsule (40) despite a permanent compression of the outer sheath (10) and/or despite a permanent elongation of the inner sheath (20) in the direction of the longitudinal axis (x).

D. The catheter device according to one of the preceding embodiments, wherein the handle (70) includes an elongated rod (81) that is slidable along the longitudinal axis (x), wherein when the locking element (80) is in its first state, the rod (81) is configured to be pressed by the traveler (76) against the locking element (80) to limit the movement of the traveler (76) in the distal direction (D), wherein a first spring element (760) connected to the traveler (76) is arranged between the traveler (76) and the rod (81) and is pretensioned against the rod (81) when the traveler (76) presses against the locking element (80).

E. The catheter device according to embodiment D, wherein the locking element (80) is configured to release the rod (81) when the locking element (80) is moved from the first state to the second state, wherein the rod (81) is pushed in the distal direction (D) by the first spring element (760).

F. The catheter device according to embodiment D or E, wherein when the locking element (80) is in the second state, the further movement of the traveler (76) in the distal direction (D) pushes the rod (81) against a stop (83) to finally limit the further movement of the traveler (76) and therewith of the capsule (40) in the distal direction (D), wherein the first spring element (760) is pretensioned by the traveler (76) against the rod (81) and a second spring element (810) is pretensioned by the rod (81) against a guiding member (75) that guides the rod (81) and forms said stop (83).

G. The catheter device according to one of the preceding embodiments, wherein the handle (70) includes an actuating element (800) configured to be manually actuated by a user, wherein the actuating element (800) is operatively connected to the locking element (80) such that the locking element (80) is moved from the first state to the second state when the actuating element (800) is actuated by a user.

H. The catheter device according to one of the preceding embodiments, wherein the handle (70) includes a third spring element (801), wherein the third spring element (801) is configured to be pretensioned against the locking element (80) when the latter is moved from the first state to the second state.

I. The catheter device according to embodiment D or according to one of the embodiments E to H if referring to embodiment D, wherein the locking element (80) includes an opening (802) having a narrow portion (802*a*) and an adjacent wider portion (802*b*), and wherein the rod (81) includes a distal portion including a narrow section (81*b*) having a diameter that is smaller than a diameter of an adjacent proximal portion of the rod (81) so that the rod (81) forms a step (81*c*), wherein when the locking element (80) is in the first state said narrow section (81*b*) of the rod (81) is arranged in the narrow portion (802*a*) of the opening (802) and the rod (81) is configured to be pressed by the traveler (76) against the locking element (80) with said step (81*c*) to limit the movement of the traveler (76) in the distal direction (D).

J. The catheter device according to embodiments D and I, wherein when the locking element (80) is moved from the first state to the second state, the rod (81) is arranged in the wide portion (802*b*) of the opening (802) so that the step (81*c*) is allowed to move through the wide portion (802*b*) of the opening (802) of the rod (81) by the action of the first spring element (760).

K. The catheter device according to embodiments D, F, and H, and according to embodiment 9 or 10, wherein, when the second spring element (810) is pretensioned, moving the traveler (76) and therewith the capsule (40) in the proximal direction (P) causes the second spring element (810) to move the rod (81) in the proximal direction (P), too, such that said narrow section (81*b*) of the rod (81) moves into the wide portion (802*b*) of the opening (802) of the locking element (80) at a certain position of the traveler (76) such that the third spring element (801) moves the locking element (80) back into the first state in which said narrow section (81*b*) of the rod (81) is arranged in the narrow portion (802*a*) of the opening (802) of the locking element (80).

L. The catheter device according to embodiment F or according to one of the embodiments G to K if referring to embodiment F, wherein the deployment knob (72) is rotatably supported on the guiding member (75) of the handle (70).

The invention claimed is:

1. A catheter device for implanting a medical implant, comprising:

a handle comprising a grip portion, a rotatable deployment knob, and a traveler, a helical groove formed in an inside of the deployment knob, an outer sheath connected to the traveler, wherein the outer sheath defines a lumen and extends along a longitudinal axis (x) of the catheter device, an inner sheath arranged in the lumen, wherein the inner sheath extends along the longitudinal axis (x), a support or connector connected to the inner sheath, the support or connector being configured to support the medical implant, a capsule connected to a distal end of the outer sheath, the capsule being configured to cover the medical implant when the medical implant is arranged on the support or the connector, wherein the traveler engages into the helical groove such that the traveler and thereby the outer sheath are moved in a proximal direction (P) along the longitudinal axis (x) with respect to the inner sheath when the deployment knob is rotated in a first rotation direction (R1), so that the capsule is pulled away from the medical implant in the proximal direction (P) to deploy the medical implant, and such that the traveler and thereby the outer sheath are moved in the distal direction (D) along the longitudinal axis (x) with respect to the inner sheath when the deployment knob is rotated in an opposite second rotation direction (R2), so that the capsule is moved over the medical implant to cover the medical implant, a rod coupled to movement of the traveler, a lock mechanism in the handle, the lock mechanism comprising a biased portion with a structural feature that engages the rod in a first default locked state to prevent distal movement of the rod, traveler, outer sheath, and capsule, wherein the first locked default state positions the rod, traveler, outer sheath, and capsule in a first distal position such that the capsule completely covers the implant when the inner and the outer sheath have not yet been permanently deformed during operation of the catheter device;

a button configured to move the structural feature into a second unlocked state to disengage the rod to permit distal movement of the rod, traveler and outer sheath, and capsule into a second distal position distally past the first distal position such that the implant is completely coverable by the capsule despite a permanent compression of the outer sheath and/or despite a permanent elongation of the inner sheath in the direction of the longitudinal axis (x).

2. The catheter device according to claim 1, a first spring between the traveler and the rod, the first spring being configured to push the rod in the distal direction (D).

3. The catheter device according to claim 2, wherein the handle comprises a second spring configured to be compressed by distal movement of the rod, traveler and outer sheath, and capsule into the second unlocked state, wherein the first spring is pretensioned by the traveler against the rod and the second spring is pretensioned by the rod against a guiding member that guides the rod and forms a stop.

4. The catheter device according to claim 1, wherein the handle comprises a third spring configured to be pretensioned against the structural feature when the structural feature is moved from the first default locked state to the second unlocked state.

5. The catheter device according to claim 4, wherein the structural feature comprises an opening having a narrow portion and an adjacent wider portion, and wherein the rod comprises a distal portion comprising a narrow section having a diameter that is smaller than a diameter of an adjacent proximal portion of the rod so that the rod forms a step, wherein when the structural feature is in the first default locked state said narrow section of the rod is arranged in the narrow portion of the opening and the rod is configured to be pressed by the traveler against the structural feature with said step to limit the movement of the rod, traveler, outer sheath, and capsule in the distal direction (D).

6. The catheter device according to claim 5, wherein when the structural feature is moved from the first default locked state to the second unlocked state, the rod is arranged in the wide portion of the opening so that the step is allowed to move through the wide portion of the opening of the rod by action of the first spring.

7. The catheter device according to claim 6, wherein, when the second spring is pretensioned, moving the traveler and therewith the capsule in the proximal direction (P) causes the second spring to also move the rod in the proximal direction (P), such that said narrow section of the rod moves into the wide portion of the opening of the structural feature at a certain position of the traveler such that the third spring moves the structural feature back into the first state in which said narrow section of the rod is arranged in the narrow portion of the opening of the structural feature.

8. The catheter device according to claim 3, wherein the deployment knob is rotatably supported on the guiding member of the handle.

9. A catheter device for implanting a medical implant, comprising:

a handle comprising a grip portion, a rotatable deployment knob, and a traveler, a helical groove formed in an inside of the deployment knob, an outer sheath connected to the traveler, wherein the outer sheath defines a lumen and extends along a longitudinal axis (x) of the catheter device, an inner sheath arranged in the lumen, wherein the inner sheath extends along the longitudinal axis (x), a support or connector connected to the inner sheath, the support or connector being configured to support the medical implant, a capsule connected to a distal end of the outer sheath, the capsule being configured to cover the medical implant when the medical implant is arranged on the support or the connector, locking means for locking the traveler, outer sheath and capsule in a first distal position such that the capsule completely covers the implant when the inner and the outer sheath have not yet been permanently deformed during operation of the catheter device; and overtravel means for unlocking the traveler to permit distal movement of the rod, traveler and outer sheath, and capsule into a second distal position distally past the first distal position such that the implant is completely coverable by the capsule despite a permanent compression of the outer sheath and/or despite a permanent elongation of the inner sheath in the direction of the longitudinal axis (x).

* * * * *